United States Patent [19]

Etheredge, III

[11] Patent Number: 5,018,532
[45] Date of Patent: May 28, 1991

[54] NOVEL PHOSPHORESCENT CONDOMS

[76] Inventor: Robert W. Etheredge, III, 5 Oakhill Rd., Natick, Mass. 01760

[21] Appl. No.: 214,308

[22] Filed: Jun. 27, 1988

[51] Int. Cl.$^5$ .............................................. A61F 6/04
[52] U.S. Cl. .................................... 128/844; 128/918; 604/349
[58] Field of Search ............... 604/346, 347, 348, 349, 604/350, 351, 352, 353; 128/830, 842–844; 250/462.1, 483.1; 116/200, 202

[56] References Cited

U.S. PATENT DOCUMENTS

| | | | |
|---|---|---|---|
| 2,536,631 | 1/1951 | Ely | 604/362 |
| 2,586,674 | 2/1952 | Lonne | 128/844 |
| 4,244,369 | 1/1981 | McAvinn et al. | 604/362 |
| 4,332,243 | 6/1982 | Gutnick | 128/844 |
| 4,432,357 | 2/1984 | Pomeranz | 128/844 |
| 4,576,156 | 3/1986 | Dyck et al. | 128/844 |
| 4,920,983 | 5/1990 | Liminez et al. | 128/844 |

FOREIGN PATENT DOCUMENTS

| | | | |
|---|---|---|---|
| 0593637 | 3/1934 | Fed. Rep. of Germany | 604/349 |
| 0033958 | 10/1973 | Japan | 604/349 |

OTHER PUBLICATIONS

Everett et al., "The Condom Book", May 1987, pp. 51–54, 130–131.

Primary Examiner—C. Fred Rosenbaum
Assistant Examiner—Mark O. Polutta
Attorney, Agent, or Firm—Alvin Isaacs

[57] ABSTRACT

Novel condoms containing a phosphorescent material which, when activated by actinic radiation, e.g. ultraviolet or visible light, will exhibit luminosity over a period of time following such exposure to actinic radiation.

11 Claims, No Drawings

NOVEL PHOSPHORESCENT CONDOMS

BACKGROUND OF THE INVENTION

The patent and other literature are replete with references to the art of making condoms as well as various materials which may be employed in condom manufacture. However, as is well understood, irrespective of the method of making and the materials employed, a condom may be described as being an elongated, generally tubular device of thin flexible material having a closed and an open end.

In general, useful materials for making condoms include natural rubber, lambskin, and synthetic elastomeric or rubbery materials. Examples of such materials mentioned in the patent literature include polyisoprene, polyurethane, copolymers of vinylidine fluoride and hexafluoropropylene, polyethylene, polypropylene glycol, crosslinked collagen, etc.

It is also well known in the art to coat or otherwise incorporate various reagents into condoms to perform specific desired functions.

While not intended to be an exhaustive survey of the patent literature, the following patents obtained upon a cursory search will nevertheless be illustrative of the state of the art.

U.S. Pat. No. 3,136,417 issued to Clinch discloses the concept of applying a thin film of lubricating oil such as silicone to the surface of a condom or similar article. Preferably, a dusting compound such as talc, mica, lycopodium, starch, corn meal, corn grits, or mixtures thereof is applied before the oil.

U.S. Pat. No. 4,119,094 issued to Micklus discloses coating a condom with PVP-polyurethane interpolymer to provide a low coefficient of friction.

U.S. Pat. No. 4,143,423 issued to Sternlieb teaches coating a condom with a water soluble chemical compound that incorporates sodium or potassium in chemical combination with a carbonate, bicarbonate, acetate, acetate dihydrate or trihydrate to provide a lubricating coating for ease of installation.

U.S. Pat. No. 4,432,357 of Pomeranz relates to a condom having deformable sealed chambers filled with a rheopexic fluid which will provide a stiffening effect to the condom as a function of increasing shear stress applied thereto during intercourse, thereby simulating an erection, even if the user does not have a complete erection.

U.S. Pat. No. 4,415,548 of Reddy discloses dispensing a migratory pharmaceutical formulation comprising a liquid nonionic surfactant spermicidal agent and a polyethylene glycol lubricant composition into the cup of the condom, whereby the formulation migrates by capillary action throughout the inner and outer surfaces of the condom.

In view of the increasing number of AIDS victims, there has been considerable notoriety of late to the use of condoms to prevent transmission of diseases during intercourse. Consequently, there is increasing concern on the part of consenting partners during intercourse, which frequently occurs in darkened rooms, for assurance that the male partner is in fact wearing or properly wearing a condom prior to and during penetration, as he alleges.

A primary task of this invention, therefore, is to provide a method for this assurance.

Another object of this invention is to provide a means for determining whether any semen has escaped during ejaculation, e.g. through pinholes or other defects in the condom manufacture, or from improper use of the condom.

These and other objects will in part be obvious and will in part appear hereinafter in the detailed description which follows.

BRIEF SUMMARY OF THE INVENTION

In accordance with this invention the aforementioned objects are accomplished by incorporating a non-toxic or innocuous phosphorescent material in the condom at some stage during or after manufacture, the phosphorescent material being present in an amount sufficient to exhibit visibly discernible luminosity over a period of time, e.g. at least 30 minutes, following exposure to actinic radiation.

DETAILED DESCRIPTION OF THE INVENTION

As previously mentioned, in accordance with this invention an effective amount of a phosphorescent material is incorporated in the condom, which material will luminesce following exposure to actinic radiation such as ultraviolet (UV), natural or incandescent light.

As used herein and in the appended claims, the term "effective amount" denotes an amount sufficient to provide visibly discernible luminescence for a desired period of time, e.g. for at least 30 minutes. Since the amount to be employed is at least in part dependent upon the luminescent nature of the material employed and is at least in part dependent upon the extent of exposure (as a function of time and intensity), it is not capable of precise quantification. However, in general it may be said that amounts of on the order of 5-30% by weight, based upon the total solids content, will be sufficient.

While phosphorescent materials are of course well known in the literature, it will of course be appreciated that for the contemplated use the material should either be non-deleterious or, if harmful, encapsulated or otherwise insulated so as to be non-deleterious, i.e. nontoxic, if it contacts the user. An illustrative phosphorescent material of this description is copper-activated zinc sulfide (ZnS:Cu) which in the reported literature on toxicology has been found to be nontoxic and nonirritating.

This phosphorescent material is at present commercially available in particle sizes ranging from 20-40 microns diameter in single and double activated forms. Other useful materials may be readily suggested to the skilled worker in the light of this disclosure.

In one preferred embodiment of this invention, the phosphorescent material is dispersed or suspended in the condom elastomer during manufacture.

For example, a particularly useful known method of condom manufacture utilizes the process known as dip coating. In this procedure, a mandrel of the desired length and diameter is employed. In general, by this procedure the mandrel made of a smooth impermeable material such as glass or ceramic is dipped into a solution of the elastomer, a thin coating of which adheres to the mandrel after removal from the coating solution and subsequently forms a coherent elastic film. While in theory a single dipping may provide a cured elastomer layer of the desired thickness, in practice a plurality of such dippings are made due to the fact that thinner or less viscous coating solutions are normally used. Consequently, it is customary in the condom art to use these thinner solutions requiring repeated dippings to form the condom of desired strength and thickness. In using the dip coating method, it will of course be appreciated that the coating adhering to the mandrel after removal is dried before the next dipping step and this procedure is repeated until completion.

To illustrate the per se known dip coating method more fully, the mandrel is dipped into a warm aqueous solution of rubber latex containing, for instance, on the order of 5–30% by weight of latex solids. The mandrel is removed and allowed to dry, preferably under mild heat to expedite the drying, in order to coalesce the latex. This dipping and drying procedure is then repeated the requisite number of times to build up the latex layer on the mandrel to the desired thickness. After the final dipping, the latex is heated to cure. The resulting latex condom may then be removed from the mandrel, e.g. by rolling it off, and is ready for packaging or any subsequent treatment, e.g. applying a lubricious coating, as described, for example, in certain of the aforementioned patents.

In accordance with one embodiment of this invention, the phosphorescent material will be dispersed in at least one of the solutions in which the mandrel is dipped in order to provide an effective amount of phosphorescent material. Each dip coating may contain the phosphorescent material, in which case the cumulative amount of phosphorescent material from the several dippings will provide the effective amount. In order to minimize the coating solutions to be used, the various dippings will be in the same coating solution containing the phosphorescent material, in which event each stratum making up the latex coating will contain the same amount of phosphorescent material. However, it will be appreciated that it is within the scope of this invention to vary the amounts or ratio of phosphorescent material in each dipping. For example, it may be desirable, when employing some phosphorescent materials, to employ minimal ratios of phosphorescent material in the inner stratum or in both the inner and outer strata.

In another preferred embodiment of this invention, the inner and outer strata will not contain any phosphorescent material at all, in which event the intermediate phosphorescent-containing strata may be said to be "sandwiched" between strata containing no phosphorescent material.

In another preferred embodiment of this invention, the phosphorescent particles are inserted within the condom itself. In this embodiment, they may simply be placed within the condom prepared in the foregoing manner or the condom may be provided with a pocket at what may be described as the leading end portion of the condom, whereby they are isolated from any physical contact with the penis which may be abrasive. In this preferred embodiment, the above-noted advantage of ascertaining that the male partner is using the condom is obtained along with the additional advantage of ascertaining whether any semen have escaped the confine of the condom after ejaculation. In other words, upon ejaculation, the semenal fluid would mix with the phosphorescent material, thereby providing a luminescent marker for the fluid. The readily detectable luminescence would thereby facilitate cleaning up or any remedial steps which might appear advisable.

The following examples show by way of illustration and not by way of limitation the preferred embodiments of this invention.

EXAMPLE 1

A ceramic mandrel of known description in the condom manufacturing art is dipped into a warm solution of rubber latex containing 20% by weight, based upon total solids of the solution, of copper-activated zinc sulfide as phosphorescent material, mean particle size, approx. 20 microns. The thus coated mandrel is removed and allowed to dry under mild heat to coalesce the latex on the mandrel. The dipping and drying steps are repeated with the same latex solution an additional four times. After the final dipping, the latex-containing mandrel is placed in an autoclave and heated to about 212° F. to cure the latex. The resulting latex condom was then rolled and slid off the mandrel.

EXAMPLE 2

Example 1 was repeated, except that the inner (first) and outer (last) coatings contained no phosphorescent material, whereby the phosphorescent material present in the middle three dip coating is sandwiched between the outer latex coatings.

EXAMPLE 3

A coating solution is prepared having the following proportions of ingredients:

| | |
|---|---|
| Tetrahydrofuran (solvent) | 100.00 gms |
| "TECOFLEX" (trademark of Thermedics Inc. for a segmented linear polyurethane) | 7.00 gms |
| ZnS:Cu | 1.75 gms |

A glass mandrel is dipped in the above solution, removed and dried at 50° C. It is then redipped four additional times in the same manner, after which the resulting condom is removed from the mandrel.

EXAMPLE 4

A conventional condom is prepared by the dip coating method. Approximately 500 mgs. of the copper-activated zinc sulfide is then inserted within the condom.

While the foregoing Examples illustrate preferred embodiments of this invention, it is to be expressly understood that the invention is not limited thereto, nor is it limited to the particular materials recited in the Examples.

For example, U.S. Pat. No. 3,553,308 issued to Kobayashi et al discloses a method for preparing polyurethane condoms employing two baths, one containing a polyurethane prepolymer component and the other containing a curing agent, wherein a mold is dipped into the two baths to form the polyurethane condom. It is contemplated that a polyurethane condom of this invention may be obtained by incorporating the phosphorescent material in either or both baths.

A procedure for preparing condoms from fish collagen is described in U.S. Pat. No. 4,406,853 of Miyata wherein a membrane is formed by dipping a mandrel twice into a dispersion of the collagen, removing the mandrel each time while spinning, neutralizing and drying. The membrane is then crosslinked and removed from the mandrel. In accordance with the present invention, the phosphorescent material may be incorporated in the collagen dispersion.

In yet another alternative embodiment, the phosphorescent material may be suspended in a coating such as a lubricant and/or spermatocide in lieu of mixing it with the elastomer as described previously.

Other means of preparing phosphorescent condoms will also be envisioned by those skilled in the art in the light of the foregoing disclosure. It is contemplated, for instance, that the phosphorescent material may be added to the feedstock for extrusion processing, added to the melt for thermoformed devices, mixed in the solvent system for solvent-based elastomers, mixed in a Banbury prior to fabrication, or even laminated to the elastomer as part of another layer.

Since certain changes may be made without departing from the scope of the invention herein described, it is intended that all matter contained in the foregoing description, including the examples, shall be taken as illustrative and not in a limiting sense.

What is claimed is:

1. In a condom comprising an elongated, generally tubular prophylactic device of thin flexible material having an inner and an outer surface, a closed end and an open end;

the improvement wherein said condom contains an effective amount of a material which, when activated by actinic radiation, will exhibit luminosity, said material exhibiting luminosity being incorporated within said thin flexible condom material, said inner and outer surfaces of said condom containing none of said material exhibiting luminosity.

2. A condom as defined in claim 1 wherein said material exhibiting luminosity comprises from about 5 to about 30 percent by weight, based upon the total solids content of said condom, of a phosphorescent material.

3. A condom as defined in claim 2 wherein said phosphorescent material comprises particles ranging from about 20 to about 40 microns in diameter.

4. A condom as defined in claim 1 wherein said thin flexible condom material comprises a rubber latex.

5. A condom as defined in claim 1 wherein said thin flexible condom material comprises polyurethane.

6. A condom comprising an elongated, generally tubular prophylactic device of thin flexible material having a closed end and an open end, said flexible material comprising a membrane consisting of inner and outer stratum walls and at least one intermediate stratum between said inner and outer stratum walls, at least one of said intermediate stratum containing an effective amount of a phosphorescent material which, when activated by actinic radiation, will exhibit luminosity over a period of time following exposure to said actinic radiation.

7. A condom as defined in claim 6 wherein said inner and outer stratum contain none of said phosphorescent material, whereby said phosphorescent material is sandwiched between said walls containing no phosphorescent material.

8. A condom as defined in claim 7 wherein said inner and outer stratum walls comprise a rubber latex.

9. A condom as defined in claim 6 wherein each said stratum of said membrane contains said phosphorescent material.

10. A condom as defined in claim 9 wherein said inner stratum contains less phosphorescent material than said intermediate stratum.

11. A condom as defined in claim 10 wherein said inner and outer stratum walls comprise a rubber latex.

* * * * *